(12) United States Patent  (10) Patent No.: US 7,641,881 B2
Steinberg  (45) Date of Patent: Jan. 5, 2010

(54) FERTILIZER PRODUCTION FROM FOSSIL FUEL WITH MINIMAL CARBON DIOXIDE EMISSION

(75) Inventor: Meyer Steinberg, Melville, NY (US)

(73) Assignee: HCE, LLC, Oakton, VA (US)

( * ) Notice: Subject to any disclaimer, the term of this patent is extended or adjusted under 35 U.S.C. 154(b) by 514 days.

(21) Appl. No.: 11/733,185

(22) Filed: Apr. 9, 2007

(65) Prior Publication Data
US 2007/0245787 A1 Oct. 25, 2007

Related U.S. Application Data

(60) Provisional application No. 60/767,496, filed on Apr. 21, 2006.

(51) Int. Cl.
C01B 31/00 (2006.01)
C01B 3/24 (2006.01)
C05C 9/00 (2006.01)
C05D 9/00 (2006.01)
C05D 9/02 (2006.01)
C05B 7/00 (2006.01)
C05B 17/00 (2006.01)
C05B 11/04 (2006.01)
C01C 1/00 (2006.01)
C01B 3/02 (2006.01)

(52) U.S. Cl. .................. 423/415.1; 423/650; 71/28; 71/31; 71/32; 71/34; 422/148; 422/906; 564/69; 252/375; 252/376

(58) Field of Classification Search ................ 71/28, 71/31, 32, 34, 44, 64; 422/148, 188, 189; 423/213.2, 239.1, 239.2, 352, 359, 422, 428, 423/544, 548, 554; 518/700, 702, 703, 704; 564/65, 66, 67, 69, 70, 73; 252/375, 376
See application file for complete search history.

(56) References Cited

U.S. PATENT DOCUMENTS

| 6,248,794 | B1 | 6/2001 | Gieskes |
| 6,334,986 | B2 | 1/2002 | Gieshoff et al. |
| 6,692,716 | B1 | 2/2004 | Phinney |
| 6,696,026 | B2 | 2/2004 | Pagani et al. |
| 6,821,311 | B1 | 11/2004 | Karonen et al. |
| 7,108,732 | B2 | 9/2006 | Sakamoto et al. |

FOREIGN PATENT DOCUMENTS

WO  WO 2089536 A1 * 11/2002

* cited by examiner

Primary Examiner—Jerry Lorengo
Assistant Examiner—Jennifer A Smith
(74) Attorney, Agent, or Firm—Louis Ventre, Jr.

(57) ABSTRACT

An ammonia and fertilizer production process is based on partial oxidation of fossil fuel, which co-produces polycarbonsuboxide. The four step process is low-cost and low-carbon-dioxide emission. It comprises the steps of reacting fossil fuel with oxygen in air and steam in an electric discharge plasma to produce a gas exit stream of polycarbonsuboxide, hydrogen with associated nitrogen (110); cooling the gas stream to condense and separate the polycarbonsuboxide as a solid polymer (120); compressing the gas stream to pressures for synthesis of ammonia (140); and, converting the gas stream to ammonia by employing a catalytic converter (150). Optional steps involve gas cleanup, which include removal of contaminants from the gas stream and adding hydrogen or nitrogen to the gas stream to adjust the ratio of hydrogen to nitrogen to three to one, respectively, prior to converting the gas stream to ammonia (130).

7 Claims, 1 Drawing Sheet

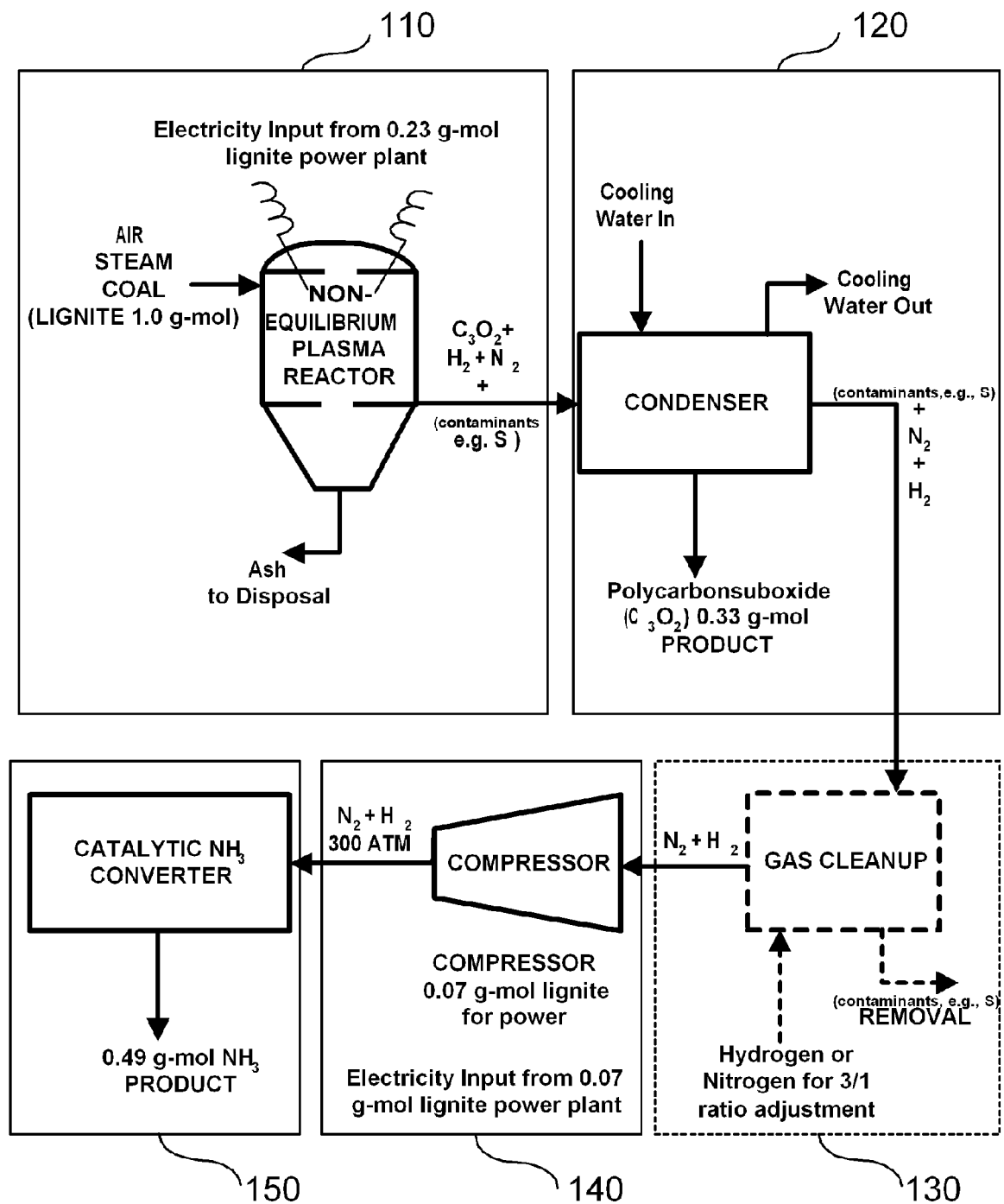

FERTILIZER PRODUCTION FROM FOSSIL FUEL WITH MINIMAL CARBON DIOXIDE EMISSION

CROSS-REFERENCE TO RELATED APPLICATIONS

Pursuant to 35 U.S.C. section 119(e), the present invention claims the benefit of the filing date of U.S. provisional application 60/767,496 filed 21 Apr. 2006, the text of which is included by reference herein.

FIELD OF INVENTION

In the field of fertilizer production, a method of producing ammonia, polycarbonsuboxide, urea and ammonium carbonate from fossil fuel at low-cost with reduced carbon dioxide emission including utilizing the carbon dioxide produced in the process.

BACKGROUND OF THE INVENTION

Fertilizers are important national and agricultural support commodities. Ammonia is a fertilizer itself, but is also used in the form of ammonia nitrate, ammonium sulfate, ammonium carbonate, urea, and other chemical forms in balanced commercial fertilizers. Ammonia is typically produced using natural gas in a process that produces carbon dioxide emissions, which contributes to global warming.

The present process enables the production of ammonia from fossil fuels, typically coal, oil or natural gas, with significantly reduced carbon dioxide release. The present invention co-produces the fertilizer and soil conditioner, polycarbonsuboxide, and permits the production of urea and ammonium carbonate with even greater reduction of carbon dioxide. The combined carbon dioxide releases from the present invention will be far less than the traditional fertilizer production methods using natural gas. Because of the coproducts created in the process, a lower cost for ammonia and fertilizer production results from the process using any fossil fuel feedstock. The largest cost reduction is obtained using a coal feedstock, which reduces costs to about one-ninth of the cost of production using conventional natural gas reforming at current feedstock prices. For this reason, the preferred embodiment uses a coal feedstock and serves as the principle example of the invention in this description.

Polycarbonsuboxide is a polymerized anhydride of malonic acid and acts as a high value organic fertilizer and soil conditioner. Polycarbonsuboxide in most soil produces humic acid. Humic acid is well known to condition soil by aiding in micronutrient ion transport, improving water penetration and retention and disaggregating clay structures.

The advanced coal to coproduct polycarbonsuboxide process has more than double (2.3) the energy consumption per ton of ammonia of the base natural gas plant but less than half the carbon dioxide emission and 2 to 4 times more coproduct than the carbon coproduct in the natural gas cracking process. If added process steps for production of urea or ammonium carbonate, carbon dioxide can be practically eliminated.

DESCRIPTION OF PRIOR ART

Conventional ammonia production processes typically employ steam reforming of natural gas to produce hydrogen and carbon monoxide. The conventional process is a contributor to global carbon dioxide emissions.

Ammonia production, which is mainly produced from natural gas, generated a total of 1.25% of the worldwide carbon dioxide emitted in 2001. Ammonia ranks about fifth among the most abundantly produced chemicals in the United States, but only about 10% of the worldwide carbon dioxide from ammonia production was produced in the United States. China generated about 25% of the total carbon dioxide emitted from ammonia production. Although the ammonia industry generates a small fraction of the worldwide carbon dioxide emissions, the quantity is not insignificant.

The conventional ammonia production process uses a natural-gas-fired tubular reactor for steam reforming, which usually employs a catalyst. The reactor tubes are heated with radiant natural gas burners. The hydrogen and carbon monoxide, also called synthesis gas, is sent to a water gas shift reactor where additional hydrogen is produced and the carbon monoxide is converted to carbon dioxide. The carbon dioxide is separated either by absorption-stripping with a solvent or by pressure swing adsorption on a sorbent to produce a clean stream of hydrogen. An air separation plant provides the nitrogen for reacting with the hydrogen in the catalytic ammonia converter. Alternatively, the nitrogen is obtained from the flue gas of the reformer by removal of the water and carbon dioxide from the combustion gas.

Overall the unit energy cost of the conventional process is about 25 million BTUs per ton of ammonia produced. This compares to about 57 million BTU's of lignite to produce a ton of ammonia with the present invention using coal as fuel feedstock. Despite the need to consume more than twice as much energy, the cost is about half and the carbon dioxide produced is about 56 to 62% less. Lower costs are possible due in part to the large price differential between coal as feedstock and natural gas as feedstock and in part due to the value of the coproducts. Lower carbon dioxide emissions are possible because the fertilizer polycarbonsuboxide is co-produced with the ammonia. The unit carbon dioxide produced in the conventional process is 1.45 tons per ton of ammonia, but can rise to 1.66 tons per ton of ammonia in older plants. This compares to 0.64 tons carbon dioxide per ton of ammonia from the process of the invention using a coal feedstock.

Further reduction of carbon dioxide emissions with the present invention are optionally achieved by process steps producing two other fertilizer products, which utilize carbon dioxide produced in ammonia production. These two fertilizer products are urea and ammonium carbonate. These process steps utilize exothermic reactions, which do not require energy input. This is notable because no energy input means no additional carbon dioxide generation. The process utilizes practically all of the carbon dioxide generated.

Accordingly, the objects of this invention are to provide a means to greatly reduce carbon dioxide emission from ammonia production, co-produce other fertilizers, utilize a fossil fuel feedstock, and significantly reduce ammonia and fertilizer production costs.

BRIEF SUMMARY OF THE INVENTION

An ammonia and fertilizer production process is based on partial oxidation of fossil fuel, which co-produces both polycarbonsuboxide and carbon. The four step process comprises the steps of reacting fossil fuel with oxygen in air and steam in an electric discharge plasma to produce a gas exit stream of polycarbonsuboxide, hydrogen with associated nitrogen; cooling the gas stream to condense and separate the polycarbonsuboxide as a solid polymer; compressing the gas stream to pressures for synthesis of ammonia; and, converting the gas stream to ammonia employing a catalyst. Optional steps involve gas cleanup, which include removal of contaminants from the gas stream and adding hydrogen or nitrogen to the gas stream to adjust the ratio of hydrogen to nitrogen to three to one, respectively, prior to converting the gas stream to ammonia.

BRIEF DESCRIPTION OF THE DRAWING

The drawing is a block diagram describing the preferred embodiment of the invention with optional steps in dashed boxes.

DETAILED DESCRIPTION

The preferred embodiment of the process with optional steps in dashed boxes is graphically described in the drawing. Each of the five blocks represents a step (110, 120, 130, 140, and 150) in the process. Some of the blocks show unit values of feed and products produced. Any rank of coal may be used in this process, but for purposes of this description, it is assumed that moisture free lignite coal is used. The ash in the coal is separated and removed in the plasma reactor. For other ranks of coal, the unit values of feed, products and coal consumed for power will vary.

The process of the invention converts fossil fuel to two fertilizers, ammonia and polycarbonsuboxide with very low carbon dioxide emission, which may be sequestered to produce a zero carbon dioxide emission process. Most of the electrical energy requirements are in the plasma reactor and the compressor. Assuming 1 gram-mole of lignite feed, then a total of about 0.3 gram-moles of coal will be needed in a power plant to generate the electrical energy for the preferred embodiment of the process.

The process steps are substantially the same for all fossil fuels. Some of the wastes are different because methane and oil do not have the same chemical pollutants. However, the principle products are the same for all fossil fuels. To simplify the discussion, and not to limit the invention, this description hereinafter concentrates on the on the preferred embodiment using a coal feedstock.

Step 110. When coal is the feedstock, the first step (110) produces sulfur dioxide as the predominant contaminant. A solid ash waste from the coal is also discharged from the plasma reactor. If 1 gram-mole of lignite coal is used as the feed material in this step, then 0.23 gram-moles of lignite coal must be consumed for electrically powering the plasma reactor. In the preferred embodiment, the plasma reactor is a non-equilibrium plasma reactor, which is well known in the art.

The stoichiometric reaction chemistry for the plasma reactor step (110) with a coal feedstock is given as follows: $2.31CH_{0.8}O_{0.2}+(0.15O_2+0.57N_2)+0.79H_2O=0.78(C_3O_2)+1.73H_2+0.57N_2$. In words, this is 2.31 moles of lignite plus 0.15 moles of oxygen from air plus 0.57 moles of nitrogen from air plus 0.79 moles of steam equals 0.78 moles of polycarbonsuboxide plus 1.73 moles of hydrogen plus 0.57 moles of nitrogen. The energy requirement for this reaction is 2.6 kilocalories per gram-mole lignite.

A lignite-fired power plant could provide electric power to plasma reactor and would require 25 Kcal/g-mol lignite feed, or 0.23 gram-moles of lignite per gram-mole of lignite feed. This consumption for power production assumes 30% plasma efficiency and 35% power efficiency.

Step 120. The gases in the gas stream produced from the plasma reactor are then cooled in the next step (120) and 0.33 gram-mole of polycarbonsuboxide per gram-mole of lignite feed is condensed as a polymer and separated as a solid product of the process. The temperature to which the gas stream is typically cooled is less than about 150 degrees Centigrade. A water-cooled condenser would typically be used, in this step (120) as shown in the drawing. The gas stream out of the condenser is composed of hydrogen and nitrogen with the contaminants, for example sulfur dioxide.

Step 130. The next step (130) is optional and is generally shown as "gas cleanup" in the drawing. This step adjusts the ratio of hydrogen to nitrogen in the gas stream to about three to one for optimal performance. From the above reaction, the ratio is already at 3 to 1 ratio, but optimizing adjustments to the ratio are optionally made by adding nitrogen or hydrogen to the gas stream. In an alternative embodiment, gas stream cleanup also includes removal of sulfur and other contaminants in gas stream. Sulfur dioxide is typically removed with an adsorbent, such as lime.

Step 140. The next step (140) is compressing the gas stream to pressures for synthesis of ammonia, which are about 300 atmospheres. The electric power needed to run the compressor can be produced by burning lignite fuel in a power plant and would consume about 0.07 gram-moles of lignite.

Step 150. The next step (150) is converting the gas stream to ammonia employing an ammonia promoted catalyst. This is a well-known process in the industry and the reaction is exothermic, which means it generates heat for process steam or other uses. The net unit production of ammonia is 0.38 gram-moles of ammonia per g-mol of lignite feed.

It requires about 2.56 tons of lignite to produce a ton of ammonia by the process of the invention. This process consumes about 57 million BTU's of lignite both as feed and as fuel for electricity production to produce a ton of ammonia. Burning 0.3 gram-moles of lignite to produce the power for the plasma reactor and the compressor produces about 0.64 tons carbon dioxide per ton of ammonia.

In alternative embodiments, process steps are added to consume carbon dioxide produced by the energy production process to generate electricity for the plasma reactor and the compressor operations. The carbon dioxide is chemically processed with some of the ammonia produced and water to manufacture the fertilizers, urea and ammonium carbonate. These steps are exothermic reactions, which do not require energy input, and thus do not generate any carbon dioxide.

The process step for the production of ammonium carbonate is given by the stoichiometric process reaction $2NH_3+CO_2+H_2O=(NH_4)_2CO_3$. In words, this is 2 moles of ammonia plus 1 mole of carbon dioxide plus 1 mole of water equals 1 mole of ammonium carbonate. For every ton of ammonia, this process step will consume 1.3 tons of carbon dioxide.

The process step for the production of urea is given by the stoichiometric process reaction $2NH_3+CO_2+H_2O=(NH_2)_2CO+2H_2O$. In words, this is 2 moles of ammonia plus 1 mole of carbon dioxide plus 1 mole of water equals 1 mole of urea and two moles of water. For every ton of ammonia, this process step will consume 1.3 tons of carbon dioxide.

The above-described embodiments including the drawings are examples of the invention and merely provide illustrations of the invention. Other embodiments will be obvious to those skilled in the art. Thus, the scope of the invention is determined by the appended claims and their legal equivalents rather than by the examples given.

What is claimed is:
1. A fertilizer production process comprising the steps of:
(a) reacting fossil fuel with oxygen in air and steam in an electric discharge plasma to produce a gas exit stream of a polycarbonsuboxide and hydrogen with associated nitrogen;

(b) cooling the gas exit stream to condense and separate the polycarbonsuboxide as a solid polymer; and (c) compressing the gas exit stream to pressures for synthesis of ammonia; and, (d) converting the gas exit stream to ammonia, employing a catalyst.

2. The fertilizer production process of claim 1 further comprising the step of adding hydrogen or nitrogen to the gas exit stream to adjust the ratio of hydrogen to nitrogen to three to one, respectively, prior to converting the gas exit stream to ammonia.

3. The fertilizer production process of claim 1 further comprising the step of removing sulfur in gas stream prior to converting the gas exit stream to ammonia.

4. The fertilizer production process of claim 1 further comprising the step of producing electrical power for the fertilizer production process by consuming a fossil fuel.

5. The fertilizer production process of claim 4 wherein the fossil fuel is selected from a group consisting of coal, natural gas and oil.

6. The fertilizer production process of claim 5 further comprising the step of capturing carbon dioxide from the consumption of fossil fuel and chemically combining it with ammonia and water to produce urea.

7. The fertilizer production process of claim 5 further comprising the step of capturing carbon dioxide from the consumption of fossil fuel and chemically combining it with ammonia and water to produce ammonium carbonate.

* * * * *